(12) United States Patent
Tamai et al.

(10) Patent No.: US 7,033,778 B2
(45) Date of Patent: Apr. 25, 2006

(54) METHODS FOR DETERMINING THE ACETYLATION LEVEL OF A PEPTIDE BASED ON SENSITIVITY OF THE PEPTIDE TO PEPTIDASE

(75) Inventors: Katsuyuki Tamai, Ina (JP); Toshiaki Miyazaki, Ina (JP); Emi Wada, Ina (JP); Ayumi Tatsuzawa, Ina (JP)

(73) Assignee: Cyclex Co., Ltd., Nagano (JP)

( * ) Notice: Subject to any disclaimer, the term of this patent is extended or adjusted under 35 U.S.C. 154(b) by 360 days.

(21) Appl. No.: 10/157,382

(22) Filed: May 29, 2002

(65) Prior Publication Data

US 2003/0082668 A1 May 1, 2003

Related U.S. Application Data

(63) Continuation-in-part of application No. PCT/JP00/08417, filed on Nov. 29, 2000.

(30) Foreign Application Priority Data

Nov. 29, 1999 (JP) ............................ 11-338565

(51) Int. Cl.
*C12Q 1/37* (2006.01)
(52) U.S. Cl. .................... 435/24; 435/69.2
(58) Field of Classification Search ............ 435/24, 435/18, 69.2
See application file for complete search history.

(56) References Cited

U.S. PATENT DOCUMENTS

| | | | | |
|---|---|---|---|---|
| 6,632,628 B1 * | 10/2003 | Olson et al. | ............... | 435/18 |
| 6,706,686 B1 * | 3/2004 | Long et al. | ............... | 514/10 |
| 2002/0061860 A1 * | 5/2002 | Li et al. | ............ | 514/44 |

FOREIGN PATENT DOCUMENTS

| EP | 0 691 409 A1 | 1/1996 |
|---|---|---|
| JP | 62-122599 | 6/1987 |
| JP | 11-318495 | 11/1999 |
| WO | WO 99/36532 | 7/1999 |

OTHER PUBLICATIONS

Hoffmann K. A Non-Isotopic Assay for Histone Deacetylase Activity. Nucleic Acids Res 27(9)2057-2058, 1999.*
Carmen A. Yeast HOS3 Forms a Novel Trichostatin A Insensitive . . . PNAS 96(22)12356-61, Oct. 26, 1999.*
K. Hoffman et al., *Nucleic Acids Research*, 27(9):2057-2058 (1999).
M. Takano et al., *J. Biochem.*, 98:1333-1340 (1985).
R. Steiner et al., *Analytical Biochemistry*, 196:120-126 (1991).
P. Pantazis et al., *The Journal of Biological Chemistry*, 256(9):4669-4675 (1981).
M. Nishikata et al., *J. Biochem.*, 343:385-391 (1999).
Product Catalog of HDAC Fluorescent Activity Assay/Drug Discovery Kit-AK-500, no date given.
A. Carmen et al., *Proc. Natl. Acad. Sci. USA*, 96(22):12356-61 (1999).
BIOSIS Accession No. PREV199800344471 (1998).
BIOSIS Accession No. PREV 198171059226 (1980).
BIOSIS Accession No. Embase Accession No. EMB-1982044905 (1981).
Witt MW, et al., J. Appl. Microbiol., 84(5), 847-851, (1998).
Matoba T. et al., Agric. Biol. Chem., 44(10), 2323-2328, (1980).
O'Donohue TL, et al., PEPTIDES, 2(3), 333-344, (1981).

* cited by examiner

*Primary Examiner*—Ralph Gitomer
(74) *Attorney, Agent, or Firm*—Peter F. Corless; Christine C. O'Day; Edwards & Angell, LLP

(57) ABSTRACT

The acetylation level of a peptide is determined utilizing the fact that the changes in the acetylation level are reflected in the sensitivity of the substrate peptide to a peptidase. This method can be used for measuring activities of deacetylase and acetylase, and also enables screening for substances that influence the activity of these enzymes. The deacetylase activity can be measured by a simple procedure according to the present invention.

25 Claims, 7 Drawing Sheets

METHODS FOR DETERMINING THE ACETYLATION LEVEL OF A PEPTIDE BASED ON SENSITIVITY OF THE PEPTIDE TO PEPTIDASE

The present application is a Continuation-in-Part of International application No. PCT/JP00/08417, filed on Nov. 29, 2000, which in turn claimed the prior benefit of Japanese Patent application No. 11-338565, filed on Nov. 29, 1999.

TECHNICAL FIELD

The present invention relates to simple methods for measuring the activity of acetylases or deacetylases, and simple methods of screening for inhibitors and accelerators of acetylases or deacetylases, as well as kits used for these methods.

BACKGROUND ART

Recently, enzymes catalyzing transfer or release of modified groups involved in phosphorylation, acetylation, and lipid or sugar chain modification, and functional proteins that serve as substrate of these enzymes are regarded as targets in the development of new drugs, such as anti-cancer agents, antimicrobial agents, and antibiotics. Among these enzymes, histone deacetylase is an excellent candidate as the target for developing new anti-cancer agents. Previous reports have demonstrated that agents, such as sodium butyrate, Trichostatin A, and Trapoxin, function as histone deacetylase inhibitors. These inhibitors were originally found as anti-fungal antibiotics or substances converting the morphology of v-sis-transformed cells to normal (Taunton, J. et al., Science Vol. 272, 408–411, 1996; Yoshida, M. et al., J. Biol. Chem. Vol. 265, 17174–17179, 1990). Subsequent studies revealed that the target of these agents was the histone deacetylase. Further, histone deacetylase inhibitors having strong antineoplastic activity as follows are known in the art:
FR901228 (Fujisawa Pharmaceutical Co.)
MS275 (Mitsui Pharmaceuticals Inc.).

These inhibitors of the histone deacetylase are known to induce expression of p21CIP, which is a Cdk inhibitor protein. However, other detailed mechanism of these inhibitors to exert carcinostatic action remains to be clarified.

Histone deacetylase plays an important role in the regulation of the expression of various genes by changing the structure of nucleosomes (Davie, J. R. and Chadee, D. N., J. Cell Biochem. (Suppl.) 30–31, 203–213, 1998). The histone deacetylase also has been reported to participate in the process of cell cycle and cell differentiation, and disturbance in their regulation is involved in some types of cancers (Kouzarides, T., Curr. Opin. Genet. Dev. Vol. 9, 40–84, 1999; Fenrick, R. and Hiebert, S. W., J. Cell Biochem. (Suppl.) 30–31, 194–202, 1998). Furthermore, histone deacetylase inhibitors, such as Trichostatin A (TSA) and suberoylanilide hydroxamic acid (SAHA), have been known to possess antineoplastic effect. Moreover, histone deacetylase inhibitors have been reported to possess activities as follows:
Inhibition of cell proliferation (Yoshida, M. et al., Bioassays Vol. 17, 423–430, 1995; Richon, V. M. et al., Proc. Natl. Acad. Sci. USA Vol. 93, 5705–5708, 1996; Richon, V. M. et al., Proc. Natl. Acad. Sci. USA. Vol. 95 3003–3007, 1998);
Induction of final differentiation (Yoshida, M., et al., Bioassays Vol. 17, 423–430, 1995; Richon, V. M. et al., Proc. Natl. Acad. Sci. USA. Vol. 93, 5705–5708, 1996);
Suppression of tumor growth in mouse model (Cohen, L. et al., Proc. AACR Vol. 39, 108, abstr. 736, 1998; Desai, D. et al., Proc. AACR Vol. 40, 2396, abstr. 362, 1999); and
Effect in the treatment of acute promyelocytic leukemia (Fenrick, R. and Hiebert, S. W., J. Cell Biochem. (Suppl.) 30–31, 194–202, 1998).

As described above, histone deacetylase inhibitors are expected as novel anti-cancer agents. Furthermore, they are also expected to function as antimicrobial substances. Thus, screening of histone deacetylase inhibitors are likely to be further carried out to discover substances with similar activities.

However, previous methods for measuring the activity of histone deacetylases are very complicated. More specifically, according to a known method, first, radiolabeled acetic acid is added to culture cell medium to metabolically radiolabel histone in cells. The histone purified from these cells is reacted with deacetylase. Following the reaction, radiolabeled acetyl groups released from the histone are extracted with ethyl acetate to measure the activity of the enzyme based on the radioactivity (Laherty, C. D. et al., Cell Vol. 89, 349–356, 1997; Hassig, C. et al., Cell Vol. 89, 341–347, 1997).

Method for measuring the activity of deacetylase without the use of radioactive substance has been also reported. According to the method, acetylated lysine residues, which have been labeled with a fluorescent substance, are used as substrates, and thus the measurement requires separtaion of the reaction product by reverse phase HPLC (Hoffmann, K. et al., Nucleic Acids Res. Vol. 27, 2057–2058, 1999).

On the other hand, important roles of enzymes that acetylate histone have been also discovered. Histone acetylase, also called histone acetyltransferase (HAT), has been revealed to regulate gene transcription through the acetylation of histones. Specifically, histones generally tightly coil DNAs to fold the DNAs to a compact structure. When the N-terminal basic amino acid, lysine residue, of a histone is acetylated, the binding with the DNA loosens, which is suggested to lead to mRNA synthesis. Method for measuring the activity of acetylase is basically carried out according to the same principle as those for measuring the activity of deacetylase.

As described above, the known methods comprise complicated procedures, and therefore it is difficult to treat multiple samples and to carry them out under various conditions. Thus, to readily conduct large-scale screening, such as those for discovering new drugs, a much more simple system without the use of radioisotopes have been desired.

Recently, the development and introduction of the combinatorial chemical library system, which enabled continuous fully-automatically synthesis of organic compounds as seeds of pharmaceutical agents, has realized the development of a system by which the screening of compounds can be achieved at faster speed. This system is entirely different from previous chemical libraries that comprise organic compounds extracted from natural material, and theoretically enables production of novel organic compounds without limitation. Today, major pharmaceutical companies around the world proactively introduce this innovative system. As a result, vast numbers of candidate compounds have been produced. Thus, much simpler methods for measuring activity of the compounds are intensely demanded to achieve a more efficient screening as ever for useful substances that may be used as pharmaceutical agents. However, most conventional methods are very complicated, and required high costs.

Conventional screening method includes the binding assay system. According to the system, the influence of a compound on the binding between proteins, such as enzymes, and the substrate thereof, low-molecular compounds and binding proteins, are determined. The binding assay system indeed provided a solution for the recent problem of efficiency in such screening. However, the system basically requires the use of radiolabeled substrates and huge investment for the introduction of the system. Moreover, it is basically impossible to estimate the level of the inhibitory activity of an enzyme reaction based on the system that utilizes intermolecular association as an index. In addition, radioisotopes are often used in this system, and as a consequence produces radioactive waste. Finally, a method of readily screening for compounds that regulate deacetylase activity is desired.

DISCLOSURE OF THE INVENTION

An objective of the present invention is to provide a simple method for assessing the acetylation level of a substrate peptide. Another objective of the present invention is to provide a method for measuring the activity of deacetylases or acetylases, which is based on the above-mentioned method. Further, another objective of the present invention is to provide a method for screening based on the method for measuring the activity, and kits used for these methods.

The present inventors contemplated that the sensitivity of peptides to an enzyme could be used to assess the acetylation level of a substrate peptide. Thus, upon vigorously studying the above-mentioned objectives, the present inventors discovered that some kind of peptidases does not cleave the substrate or the activity to cleave the substrate is significantly lowered when the substrate peptide is acetylated. The present inventors conceived that this phenomenon may be applicable for detecting the activity of deacetylase and acetylase, and thus completed the present invention.

Namely, the present invention relates to the following method for determining the acetylation level of a peptide. Further, the present invention relates to a method for measuring the activity of acetylase or deacetylase, and a method of screening for compounds that influences these enzyme activities based on the afore-mentioned method.

(1) a method for determining the acetylation level of a peptide, which comprises the step of detecting the changes in the acetylation level of the peptide using, as an index, the changes of the cleaving activity of a peptidase that uses the peptide as a substrate;

(2) a method for measuring the deacetylase activity or acetylase activity in a sample comprising the steps of:
(a) contacting a substrate peptide with the sample under a condition necessary for deacetylation by a deacetylase or for acetylation by an acetylase; and
(b) determining the acetylation level of said substrate peptide through detecting the changes in the acetylation level of said substrate peptide using, as an index, the changes in the cleaving activity of the peptidase that utilizes the peptide as a substrate;

(3) the method according to (2), wherein the deacetylase acts on an acetyl group that is introduced in the ε-amino group of a lysine residue;

(4) the method according to (3), wherein the deacetylase is histone deacetylase;

(5) the method according to (4), wherein the histone deacetylase is selected from the group consisting of HDAC1, HDAC2, HDAC3, Sir2, and a homologue of them;

(6) the method according to (1), wherein the peptidase is at least one of the peptidases selected from the group consisting of lysylendopeptidase, endoproteinase Lys-C, plasmin, calpain, metalloendopeptidase, and *Armillaria mellea* protease;

(7) the method according to (2), wherein the substrate peptide is labeled with a substance whose signal level changes upon cleavage of the peptide by a peptidase;

(8) the method according to (7), wherein the substrate peptide is labeled with a dye and emits a signal by the cleavage through the peptidase;

(9) the method according to (8), wherein the dye is a fluorescent substance, and the signal is a fluorescent signal;

(10) the method according to (6), wherein the substrate peptide comprises an acetylated lysine residue;

(11) the method according to (10), wherein the peptidase is a lysylendopeptidase;

(12) a reagent kit for measuring the activity of an acetylase or deacetylase, which comprises:
(a) a substrate peptide; and
(b) a peptidase whose activity of cleaving substrate peptides changes upon the changes of the acetylation level of the substrate peptide;

(13) a method of screening for compounds that inhibit or enhance the deacetylase activity, wherein the changes of the acetylation level of a substrate peptide is detected using the changes in the cleavage activity of the peptidase upon acetylation of the substrate peptide as an index, which method comprises the steps of:
(a) contacting the acetylated substrate peptide with the deacetylase in the presence of a test compound under a condition necessary for deacetylation;
(b) detecting the changes in the acetylation level of the substrate peptide; and
(c) selecting the compound that decreases or increases the deacetylation level of the substrate relative to the deacetylation level of the substrate in the absence of the test compound;

(14) a reagent kit for screening for compounds that inhibit or enhance the deacetylase activity, which comprises:
(a) a substrate peptide;
(b) a deacetylase; and
(c) a peptidase whose activity of cleaving the substrate peptide changes upon the changes of the acetylation level of the substrate peptide; and

(15) a peptide substrate that is used for measuring the activity of an enzyme that alters the acetylation level of a peptide, wherein the substrate comprises an amino acid residue that is acetylated or deacetylated by said enzyme, and wherein the sensitivity of the peptidase changes depending on the acetylation level of the amino acid residue.

Further, the present invention relates to the use of a peptide to produce the above-mentioned peptide substrate that is used for measuring the enzyme activity; wherein the peptide comprises an amino acid residue that is acetylated or deacetylated by an enzyme, which alters the acetylation level of the peptide, and the sensitivity of the peptidase to the peptide changes depending on the acetylation level of the amino acid residue in the peptide.

As used herein, the term "peptide" refers to compounds comprising two or more amino acids linked by peptide bonds; and there is no limitation on the chain length of the peptide. Accordingly, as used herein, the term "acetylase" refers to enzymes that catalyze the reaction by which an acetyl group ($CH_3CO-$) is transferred from a certain substance (for example, acetyl-CoA) to a peptide. The term "deacetylase" refers to enzymes releasing an acetyl group from an acetylated peptide. Further, as used herein, "peptidase" refers to enzymes that use peptides as the substrate and hydrolyze the peptide bonds of a peptide. In general, "peptidase" sometimes refers to enzymes acting on a peptide substrate with a relatively low molecular weight. However, as used herein, the term "peptidase" refers to enzymes that act on peptides irrespective of the molecular weight, and includes proteins. Thus, the "peptidase" of the present invention includes "protein degradation enzymes", "proteases", "proteinases", and "peptide hydrolases". The term "peptide cleaving activity", as used herein, refers to the activity of the enzyme to hydrolyze peptide bonds within substrate peptides.

Further, following abbreviations are used herein.
DMSO: dimethyl sulfoxide,
AFC: 7-Amino-4-trifluoromethyl coumarin,
p-NA: para-nitroaniline,
(Ac) Lys: $N^\epsilon$-acetyl lysine ($\epsilon$-acetylated lysine)
Boc: t-butyloxycarbonyl residue,
MCA: $\alpha$-(4-methyl-coumaryl-7-amide),
AMC: 7-amino-4-methyl-coumarin,
MOAc-Arg-Pro-Gly-Leu-(Ac)Lys-Pro-Lys(Dnp)-$NH_2$:
 (methyloxycoumarin-4-yl)acetyl-L-arginyl-L-prolyl-L-glycyl-L-leu cyl-$N^\epsilon$-acetyl-L-lysyl-prolyl-$N^\epsilon$-(2,4-dinitrophenyl)-L-lysine amide,
MOAc-Leu-Pro-(Ac) Lys-Leu-$A_2$pr (Dnp)-Pro-Arg-$NH_2$:
 (methyloxycoumarin-4-yl)acetyl-L-leucyl-L-prolyl-N$\epsilon$-acetyl-L-lysi 1-[N3-(2,4-dinitrophenyl)-L-2,3-diaminopropionyl]-L-prolyl-L-arg inine amide.

As used herein, the term "acetylation level" refers not only to the percentage of acetylated peptide within a substrate peptide but also to the degree of acetylation within a substrate peptide molecule. Thus, for example, "an increase in the acetylation level of a substrate peptide" refers to both situations wherein the percentage of acetylated peptide increases and wherein the number of acetylated sites in the substrate peptide increases.

First, the present invention relates to a method for determining the acetylation level of a peptide, which comprises the step of detecting the changes in the acetylation level of the peptide using, as an index, the changes of the cleavage activity of a peptidase that uses the peptide as a substrate.

Further, the method for determining the acetylation level of the present invention can be used to measure the activity of an acetylase and deacetylase. Specifically, the present invention relates to methods for measuring the activity of a deacetylase or acetylase that utilizes the method for determining the acetylation level of a peptide using, as an index, the changes in the cleaving activity of a peptidase. The method for measuring the activity of a deacetylase or acetylase of the present invention comprises the steps of: (a) contacting a substrate peptide with the sample under a condition necessary for deacetylation by a deacetylase or for acetylation by an acetylase; and (b) determining the acetylation level of said substrate peptide through detecting the changes in the acetylation level of said substrate peptide using, as an index, the changes in the cleavage activity of the peptidase that utilizes the peptide as a substrate.

Enzymes whose peptide-cleaving activity changes upon the changes in the acetylation level of the substrate peptide is used as the peptidase of the present invention. The present inventors newly discovered that the changes in the acetylation level of a peptide can be assessed using the changes in the sensitivity to a peptidase of the peptide as an index.

Peptidases that are used in the present invention include, for example, lysylendopeptidase, endoproteinase Lys-C, plasmin, calpain, trypsin, and so on. When the $\epsilon$ amino group of the lysine residue in the substrate peptide is acetylated, the peptidases do not cleave these substrate peptide or the cleavage activity thereof is significantly reduced.

The lysylendopeptidase is a particularly stable enzyme, and thus is one of the peptidases preferably used in the present invention. The lysylendopeptidase is a peptidase that cleaves a peptide on the C-terminal side of a lysine residue in the peptide, and its cleaving activity is significantly decreased due to the acetylation of the lysine residue.

An exemplary means for detecting the changes in the cleaving activity of the above-mentioned peptidase includes a method wherein the substrate peptide is labeled with a substance, whose signal level changes upon cleavage of the peptide, and comprises the step of measuring the signal that changes after the cleavage by the peptidase. Specifically, for example, the substrate peptide is labeled with a fluorescent substance whose emission wavelength differs depending on the presence or absence of a linkage between the substance and a peptide, and the changes in the fluorescence intensity can be measured with fluorescence spectrophotometer.

In addition, methods for detecting the cleavage of the substrate peptide include detection systems, such as high-performance liquid chromatography (HPLC), thin-layer chromatography (TLC), mass spectrometry obtained by mass spectrometer, and so on.

When a deacetylase activity is measured according to the method of the present invention, a peptide comprising amino acids that are previously acetylated is used as the substrate peptide. For example, histone deacetylase is known as an enzyme that catalyzes a reaction wherein acetyl groups are released from peptides whose lysine residues are acetylated. Thus, when the histone deacetylase is the subject deacetylase to be measured according to the invention, peptides comprising lysine residues with acetylated $\epsilon$-amino group are used in the measurement.

There is no limitation on the type of structure of the substrate peptide of the present invention so long as the substrate peptide comprises a peptide bond that can be cleaved by the peptidase and wherein the cleavage activity reflects the acetylation level of the substrate peptide. The substrate peptides of the present invention include naturally occurring peptides, peptides prepared by genetic recombination techniques, and synthetic peptides. The peptides may be fused with other peptides (for example, glutathione-S-transferase) for convenience of purification, etc. Further, the peptide may comprise structural units other than amino acids so long as it serves as the substrate for deacetylase (or acetylase) and peptidase.

The substrate peptide of the present invention can be synthesized according to conventional methods. Typically, the synthesis of a peptide is achieved by adding amino acids, residue by residue, from the carboxyl terminus of the amino acid sequence of interest. Further, some of the peptide fragments synthesized in that was may be linked together. To carry out the measurement or screening for a deacetylase activity of the present invention, the substrate peptide needs to be acetylated beforehand to the reaction. An exemplary method of amino acid acetylation includes acetylation of amino acids, whose $\alpha$ amino groups and side-chain amino groups are blocked with protecting groups, with acetic anhydride, N-hydroxysuccinimide acetate, and so on. Then, these acetylated amino acids are used to synthesize peptides comprising acetylated lysine residues according to the solid-phase method. Generally, acetylated peptides can be synthesized by peptide synthesizer according to the Fmoc method. For example, commercial suppliers, who provide custom peptide synthesis services, synthesize peptides of arbitrary amino acid sequences comprising residues acetylated at arbitrary positions.

Peptides that serve as substrates for deacetylases include the following peptides, which are labeled with fluorescent substances.

Boc-Val-Leu-(Ac)Lys-MCA

Boc-Glu-Lys-(Ac)Lys-MCA

Herein, Boc represents a protecting group for the amino group at the $N^\alpha$ position of Val or Glu. MCA is a fluorescent substance; and the $\epsilon$-amino group of the flanking lysine residue is acetylated. When these peptides are cleaved at the carboxyl-terminal side of the lysine residue, they release AMC. Since the emission wavelength of the released AMC differs from that of peptidyl-MCA, the quantity of cleaved substrates can be determined using the fluorescence intensity of AMC as an index.

Specifically, first, an acetylated substrate peptide is reacted to a subject deacetylase. When the acetyl group is released from the lysine residue, the substrate is cleaved by the above-mentioned peptidase. The deacetylase activity can be measured as the quantity of substrate cleaved according to the above-mentioned method. More specifically, in the first reaction, the lysine residue is deacetylated; and in the subsequent second reaction, proteolysis (peptide bond cleavage reaction) is conducted to convert the deacetylation level of the lysine residue in the first reaction to the level of proteolysis in the second reaction.

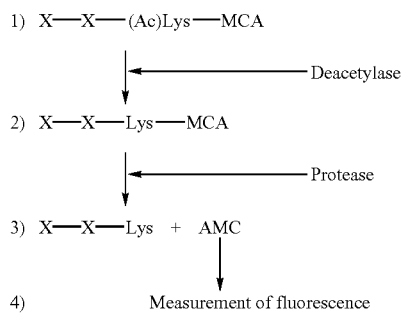

(wherein X represents an arbitrary amino acid residue.)

The procedure for measuring the histone deacetylase activity using the above-mentioned substrate peptide, Boc-Val-Leu-(Ac)Lys-MCA, is described below.

First, a substrate peptide is added to reaction buffer. The solution is poured into the wells of a microplate for fluorometry and the plate is incubated. Next, an aliquot of histone deacetylase solution is added to each well, and subjected to deacetylation for a given length of time, typically for 60 minutes. An aliquot of peptidase solution and peptidase reaction buffer is added to each well, and then the fluorescence intensity of the solution is regularly measured, typically every 150 seconds, with fluorescence microplate reader.

As shown above, X-X-(Ac) Lys-MCA may be used as the fluorescent substance-labeled peptide. However, any other fluorescent substances (for example, AFC) can be used so long as it provides a difference in the emission wavelength between the peptidyl-fluorescent substance, i.e. the substrate, and the fluorescent substance, i.e. the reaction product.

Alternatively, the substrate peptide may be previously labeled with a fluorescent substance and a quenching substance. Then, the peptide is cleaved to allow the generation of fluorescence.

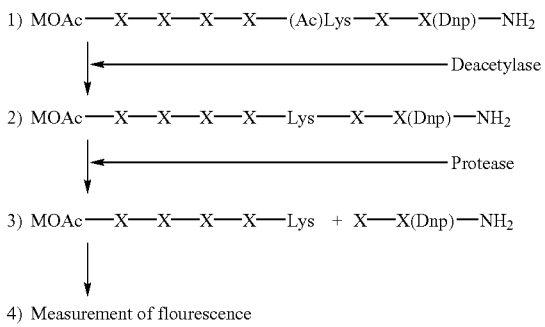

(wherein X represents an arbitrary amino acid residue.)

A fluorescent substance used for this purpose should have fluorescence, which is quenched due to the existence of an intermolecular quencher group; specific examples include MOAc, Nma (N-methylanthranilic acid), etc. Further, a quencher group should have the characteristic to quench the fluorescence of a fluorescent group within the same peptide molecule; specific examples include Dnp, and so on. A substrate in this case is exemplified by the following peptides:

MOAc-Arg-Pro-Gly-Leu-(Ac)Lys-Pro-Lys(Dnp)-NH$_2$ (SEQ ID NO: 1); and

MOAc-Leu-Pro-(Ac)Lys-Leu-A$_2$pr(Dnp)-Pro-Arg-NH$_2$ (SEQ ID NO: 2).

MOAc is a fluorescent substance and Dnp is a quenching substance. The lysine residue located between these two substances is acetylated. The fluorescence intensity of these substrates is low due to the existence of a quenching substance within the molecule. However, the fluorescence intensity is enhanced when the peptide is cleaved on the amino-terminal side of the lysine residue by a peptidase. This allows measurement of the quantity of the cleaved substrate peptide.

Alternatively, the substrate peptide may be labeled with a dye whose absorption characteristic changes upon the cleavage of the peptide. Such changes in the absorption characteristic can be detected with spectrophotometer. A substrate peptide with such characteristic includes the peptide X-X-(Ac) Lys-pNA, which is labeled with the dye p-NA.

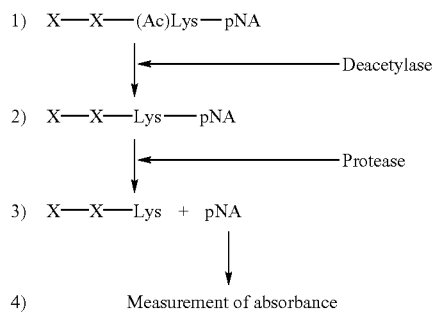

(wherein X represents an arbitrary amino acid residue.)

The above-mentioned peptidase cleaves a peptide at the carboxyl terminal side of a lysine. However, peptidases that cleave peptides at the amino terminal side of a lysine can be also used. Such peptidases include, for example, metalloendopeptidase, protease from *Armillaria mellea*, and so on. According to the method, the same fluorescent substance-labeled substrate peptide as that in the above-mentioned fluorescence quenching method should be used as the substrate peptide.

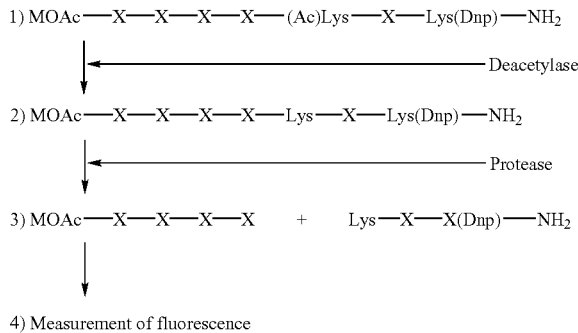

4) Measurement of fluorescence (wherein X represents an arbitrary amino acid residue.)

The above method for labeling a peptide with fluorescent substances, quenching substances, and dyes, is already known in the art, and thus, can be conducted according to conventional methods.

The above-mentioned histone deacetylase can be exemplified as the deacetylase, wherein the activity of the deacetylase can be measured according to method of the present invention. For example, HDAC1, HDAC2, HDAC3, Sir2, and such have been reported as histone deacetylase. Also, the deacetylase activities of the homologues of these histone deacetylases can be measured by the method of the present invention. Herein, a homologue of the histone deacetylase includes these histone deacetylase that is derived from non-human organisms and that has a deacetylase activity, and a mutant thereof. As describe in Example, RPD3, YY-1BP, and SIRT1 have been reported as the homologues.

Homologues of a polynucleotide encoding the above-mentioned histone deacetylase include polynucleotides that both encode a polypeptide having a deacetylase activity and comprise the amino acid sequence of the above-mentioned histone deacetylase in which one or more amino acids are deleted, substituted, inserted, and/or added. One skilled in the art can properly introduce substitution, deletion, insertion, and/or addition mutation into the polynucleotide encoding the above-mentioned histone deacetylase, by site-specific mutagenesis (Nucleic Acid Res. 10, pp. 6487 (1982), Methods in Enzymol. 100, pp. 448 (1983); Molecular Cloning 2nd Ed., Cold Spring Harbor Laboratory Press (1989), PCR: A Practical Approach, IRL Press, pp. 200 (1991)).

In addition, homologues of a polynucleotide encoding the above-mentioned histone deacetylase include polynucleotides hybridizing under stringent conditions to the polynucleotides that comprise the nucleotide sequence encoding the above-mentioned histone deacetylase, as well as those encoding a polypeptide having a deacetylase activity. The phrase "polynucleotide hybridizing under stringent conditions" refers to a polynucleotide hybridizing to a probe nucleotide that has one or more segments of at least 20 consecutive nucleotides, preferably at least 30 consecutive nucleotides, for example, 40, 60, or 100 consecutive nucleotides, arbitrarily selected from the sequence encoding the above-mentioned histone deacetylase, using, for example, ECL Direct Nucleic Acid Labeling and Detection System (Amersham-Pharmacia Biotech) under conditions recommended in the attached manual (washing with the primary wash buffer containing 0.5×SSC at 42° C.). Also included in the invention is a polynucleotide that hybridizes under high stringency conditions to the nucleotide sequence encoding the above-mentioned histone deacetylase or a segment thereof as described herein. "High stringency conditions" refers to hybridization in 6×SSC at about 45° C., followed by one or more washes in 0.2×SSC, 0.1% SDS at 65° C.

Furthermore, a homologue of a polynucleotide encoding the above-mentioned histone deacetylase includes a polynucleotide encoding a polypeptide exhibiting an identity of at least 70%, preferably at least 80% or 90%, more preferably 95% or more to the amino acid sequence of the above-mentioned histone deacetylase. As used herein, "percent identity" of two amino acid sequences or of two nucleic acids is determined using the algorithm of Karlin and Altschul (Proc. Natl. Acad. Sci. USA 87: 2264–2268, 1990) modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res. 25: 3389–3402, 1997). When utilizing BLAST and Gapped BLAST programs, the default parameters of the respective programs (e.g, XBLAST and NBLAST) are used. Homology search of protein can be readily performed, for example, via Internet, for example, in databases related to amino acid sequences of protein, such as SWISS-PROT, PIR, and such; databases related to DNAs, such as DDBJ, EMBL, or GenBank, and such; databases related to deduced amino acid sequences based on DNA sequences; and such using programs, such as BLAST, FASTA, etc.

Homologues of the above-mentioned histone deacetylase may comprise the amino acid sequence of the above-mentioned histone deacetylase in which one or more amino acids are deleted, substituted, inserted, and/or added, wherein said histone deacetylase is functionally equivalent to the polypeptide consisting of the amino acid sequence of the above-mentioned histone deacetylase. According to the present invention, "polypeptides functionally equivalent to the polypeptide consisting of the amino acid sequence of the above-mentioned histone deacetylase" are those polypeptides having a deacetylase activity. One skilled in the art can readily obtain a polynucleotide encoding such homologues of the above-mentioned histone deacetylase by properly introducing substitution, deletion, insertion, and/or addition mutation into the polynucleotide encoding the above-mentioned histone deacetylase by site-specific mutagenesis (Nucleic Acid Res. 10, pp. 6487 (1982), Methods in Enzymol. 100, pp. 448 (1983); Molecular Cloning 2nd Ed., Cold Spring Harbor Laboratory Press (1989), PCR: A Practical Approach IRL Press pp. 200 (1991)) or the like. A homologue of the above-mentioned histone deacetylase can be obtained by introducing, into a host, a polynucleotide encoding the homologue of the above-mentioned histone deacetylase and expressing it in the host.

The number of amino acids that are mutated is not particularly restricted, as long as the histone deacetylase activity is maintained. Normally, it is within 50 amino acids, preferably within 30 amino acids, more preferably within 10 amino acids, and even more preferably within 3 amino acids. The site of mutation may be any site, as long as the histone deacetylase activity is maintained.

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Furthermore, homologues of the above-mentioned histone deacetylase include polypeptides exhibiting percent identity of at least 70%, preferably at least 80% or 90%, more preferably 95% or more to the amino acid sequence of the above-mentioned histone deacetylase. Homology search of protein can readily be performed, for example, via the Internet, for example, in databases related to amino acid sequences of protein, such as SWISS-PROT, PIR, and such; databases related to DNA sequences, such as DDBJ, EMBL, GenBank, and such; databases related to deduced amino acid sequences based on DNA sequences; and such by using programs, such as BLAST, FASTA, etc.

The acetylase activity can be also measured by the same method as that used for the measurement of the deacetylase activity. According to the method, peptides wherein the lysine residues are not acetylated are used as the substrate. Following the reaction of the substrate peptide with acetylase, the cleaving activity of a peptidase against the substrate peptide is measured. The activity of the acetylase can be measured based on the changes in the cleavage activity of the peptidase, due to the fact that a peptide with acetylated lysine is not cleaved by a peptidase. Thus, the only difference between the measurement of deacetylase activity and acetylase activity is the presence/absence of acetylation in the substrate peptide.

The acetylases, whose activity can be measured according to the present invention, include GCN5, CBP/p300, TIP60, SRC1, AIB1, ACTR, and so on.

To avoid shortage of the substrate peptide relative to the predicted enzyme activity, it is preferable to use an excess amount of the substrate peptides in the present invention. Specifically, in order to determine the deacetylase activity of a general biological sample, such as cell nuclear extract, the concentration of the peptide to be used in the reaction is typically 1 to 200 µM, and preferably 20 to 50 µM. On the other hand, the concentration of the peptidase can be adjusted mainly depending on the quantity of the used substrate peptide. Typically, the amount of the peptidase is adjusted according to the predicted quantity of the generated substrate peptide so as to realize enough cleavage of the substrate peptide under a given condition. Preferably, a peptidase activity that realizes, for example, even when all the used substrate peptides are deacetylated and thus can be cleaved by the peptidase, sufficient cleavage of the peptide under a give assay condition is included in the reaction. Specifically, when lysylendopeptidase and substrate peptide at a concentration of about 20 to 50 µM is used in the reaction, the quantity of peptidase to be used is, for example, typically $1 \times 10^{-6}$ to $1 \times 10^{-4}$ AU, preferably $2.5 \times 10^{-5}$ to $7.5 \times 10^{-5}$ AU. The pH for the reaction with the deacetylase or acetylase can be selected by taking the optimal pH of the subject enzyme into consideration. For example, when the activity of the histone deacetylase is measured, the pH is typically adjusted to pH 6.0 to 8.5, preferably to pH 6.8 to 7.8. The reaction buffer can be selected from those giving the above-mentioned pH. For example, Tris-HCl, Hepes-KOH, and so on can be used in the method of the present invention. More specifically, for example, 25 mM Tris HCl, pH 7.5 can be used. It is preferable to add salts and preservatives, which are required for the expression of the enzyme activity, in the reaction solution. For example, 2 mM mercaptoethanol is preferably added to the reaction of the histone deacetylase.

These methods for measuring the acetylase activity and deacetylase activity can be used in the screening for inhibitors or accelerators of the acetylase and deacetylase, respectively. Thus, the present invention also relates to a method of screening for compounds that inhibit or enhance the activity of an acetylase or deacetylase.

The method of screening for compounds that inhibit or enhance the activity of a deacetylase of the present invention comprises the steps of:

(a) contacting an acetylated substrate peptide with a deacetylase in the presence of a test compound under a condition required for deacetylation;

(b) detecting the changes in the acetylation level of the substrate peptide; and (c) selecting the compound that decreases or increases the deacetylation level of the substrate relative to the deacetylation level of the substrate in the absence of the test compound. Test compounds to be used in this screening method include, for example, peptides; low-molecular-weight synthetic compounds; cell extracts derived from animals, plants or bacteria; cell culture supernatants; and such, but the present invention is not limited to these examples. The test compound may be added to the deacetylase prior to the enzyme reaction or at the start of the enzyme reaction.

The screening method of the present invention is carried out by incubating a sufficient amount of deacetylase (or acetylase) that realizes the deacetylation (or acetylation) of the substrate peptide under a condition suitable for the desired enzyme reaction. Specifically, for example, when the concentration of histone deacetylase is 10 to 30 U, substrate peptide at a concentration of 20 to 50 µM and lysylendopeptidase at a concentration of $2.5 \times 10^{-5}$ to $7.5 \times 10^{-5}$ AU is added to the reaction. The condition for measuring the enzyme activity described above, can be also applied for this enzyme reaction. 1 U of the histone deacetylase is defined herein as the quantity of crude histone deacetylase obtained from 1000 cells of human culture cell line MCF7.

Both steps of contacting the substrate peptide with the deacetylase and detecting the changes in the acetylation level of the substrate peptide can be achieved by the same procedure as those used in the above-mentioned method for measuring the activity of a deacetylase. When the acetylation level of the substrate peptide is lower than that detected in the absence of a test compound (control), the test compound used in the screening is determined to enhance the deacetylase activity. On the other hand, when the acetylation level of the substrate peptide is higher, the test compound used in the screening is determined to inhibit the deacetylase activity. When cell extracts from animals, plants or bacteria, or cell culture supernatants are used as the test compound, the single compound therein that enhances or inhibits the activity of the deacetylase can be specified by fractionating the test compound and subjecting each of the fractions to the detection. The fractionation can be performed by various chromatographic procedures, or others.

Furthermore, the present invention relates to kits for measuring the activity of a deacetylase and screening for compounds that inhibit or enhance the deacetylase activity described above. Moreover, the present invention relates to kits for measuring the activity of an acetylase and screening for compounds that inhibit or enhance the acetylase activity described above.

The kit according to the present invention comprises: (a) a substrate peptide; (b) a deacetylase (or acetylase); and (c) a peptidase whose activity of cleaving said substrate peptide changes upon the changes of the acetylation level of the substrate peptide. The kit according to the present invention may also comprise a test compound. A previously acetylated substrate peptide is used for the measurement of the activity of deacetylase. On the other hand, when the activity of a acetylase is measured, non-acetylated peptides should be used as the substrate. The substrate peptide may be labeled as described above. Typically, each component, (a) the substrate peptide, (b) the deacetylase (or acetylase), and (c) the peptidase whose activity of cleaving said substrate peptide changes upon the changes of the acetylation level of the substrate peptide, of the kit according to the present invention is packaged separately.

Respective components of the kit of the present invention are combined so as to realize a final concentration that is suitable for the reaction. Further, in addition to these components, the kit may comprise buffer that gives a condition suitable for the reaction. The enzyme preparation and the substrate peptide may be combined with other components that stabilize proteins. For example, it is preferable to add BSA to the preparation at a final concentration of about 1% and polyols, such as sucrose and fructose, at a final concentration of 0.2 to 10%, preferably 1% as agents preventing protein denaturation after lyophilization.

Each component of the kit according to the present invention can be provided in liquid form or dried form. Detergents, preservatives, buffers, and so on, commonly used in the art may be added to the components so long as they do not inhibit the measurement of the deacetylase activity.

Compounds that inhibit the deacetylase activity, which can be selected according to the method for screening of the present invention, are useful as candidate compounds for antimicrobial substances, anti-cancer agents, and so on.

For example, fusion between histone acetyltransferase, histone deacetylase, or proteins relating thereto and proteins having DNA binding ability due to genetic translocation is observed in patients of leukemia. Specifically, fusion proteins, such as AML1-MTG8 (Kitabayashi I. et al., Mol. Cell Biol. 18: 2, 846–58, "The AML1-ATG8 leukemic fusion protein forms complex with a novel member of the MTG8 (ETO/CDR) family, MTGR1." 1998 February); and PML-RARα (Kakizuka A. et al., Cell 23; 66(4): 663–74, "Chromosomal translocation t (15; 17) in human acute promyelocytic leukemia fuses RAR alpha with a novel putative transcription factor, PML." 1991 August; de The H. et al., Cell 23; 66(4): 675–84, 1991 August "The PML-RAR alpha fusion mRNA generated by the t (15; 17) translocation in acute promyclocytic leukemia encodes a functionally altered RAR."), have been discovered. Due to the reaction of the deacetylase on MTG8 and RARα, components of the fusion protein, i.e. the promoter region of genes required for leukocyte differentiation, is deacetylated, and thus the transcription of the gene can't be initiated. As a result, leukocyte differentiation is arrested, which is assumed to cause the onset of leukemia. As a matter of fact, deacetylase inhibitors are known to be effective for the treatment of some types of leukemia. This is ascribed to the fact that the differentiation of leukemic cells is induced by the deacetylase inhibitors.

As described above, the activity of deacetylase is closely associated with the process of canceration in leukemia. Thus, measurement of the deacetylase activity is useful in the diagnosis of leukemia. Moreover, the inhibition of the activity of the deacetylase directly leads to inhibit the process of canceration in leukemia. Thus, compounds inhibiting the deacetylase activity, which can be obtained by the screening of the present invention, are useful for the treatment of leukemia.

In addition, compounds inhibiting the activity of acetyltransferase (HAT), which can be obtained by the screening method of the present invention, are useful for suppressing virus propagation. For example, an acetyltransferase called TIP60 is known in the art. TIP60 is a protein that was identified as the HIV-1 interacting protein, and is known to induce the activation of viral gene transcription mediated by Tat of HIV (Kamine J. et al., Virology 15; 216(2): 357–66, 1996 February "Identification of a cellular protein that specifically interacts with the essential cysteine region of the HIV-1 Tat transactivator."). Further, CBP and p300, which are proteins having the HAT activity, are known to be essential for the activation of HIV-1 Tat (Marzio G., Proc. Natl. Acad. Sci. USA. 10; 95 (23): 13519–24, 1998 November, "HIV-1 tat transactivator recruits p300 and CREB-binding protein histone acetyltransferase to the viral promoter."). Actually, the HAT activity is recovered from cell extract together with Tat, and the binding to CBP/p300 was of proteins that have the HAT activity is also demonstrated. Further, the expression of CBP/p300 has been reported to induce transcriptional activation from the LTR of HIV-1 that has been integrated into host genome (Benkirane M. et al., J. Biol. Chem. 18; 273(38): 24898–905, 1998 September, "Activation of integrated provirus requires histone acetyltransferase. p300 and P/CAF are coactivators for HIV-1 Tat."). Finally, compounds that inhibit the activity of proteins having HAT activity, such as TIP60, CBP, and p300, suppresses the transcription of viral genes, and thus can be used for the treatment of HIV-1.

Herein, "%" for concentration denotes weight per volume percent unless otherwise specified.

Any patents, patent applications, and publications cited herein are incorporated by reference.

BEST MODE FOR CARRYING OUT THE INVENTION

Figure 1:
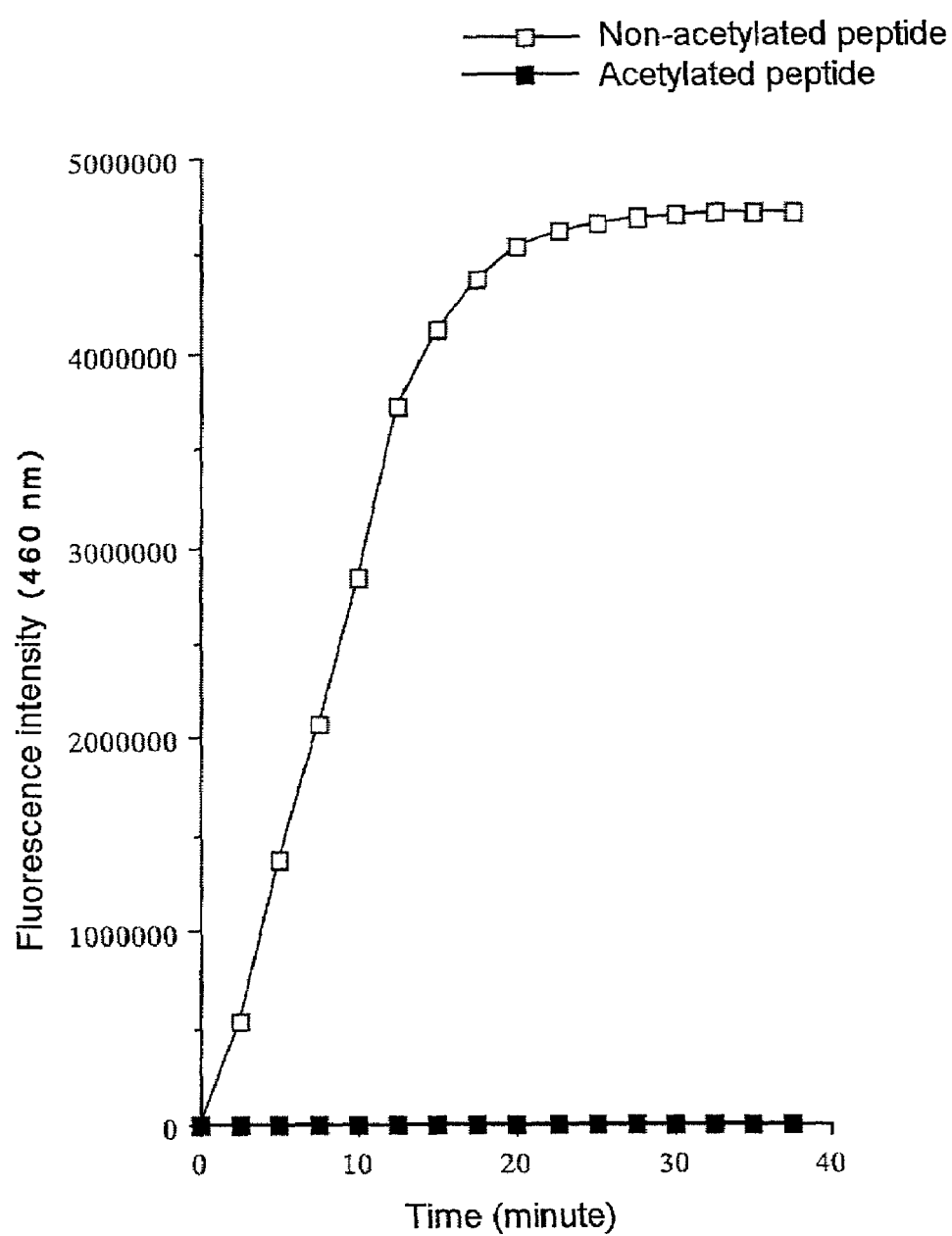
FIG. 1 depicts a graph comparing the peptide cleavage activity of lysylendopeptidase using acetylated or non-acetylated peptides as the substrate.

The present invention is illustrated in detail below with reference to Examples, but is not to be construed as being limited thereto.

EXAMPLE 1

Preparation and Purification of Recombinant Histone Deacetylase by Gene Recombination (1) Isolation of the Histone Deacetylase Gene by RT-PCR Today, three types of histone deacetylase genes have been reported: HDAC1/RPD3 (Taunton, J. et al., Science Vol. 272, 408–411, 1996; Rundlett, S. E. et al., Proc. Natl. Acad. Sci. USA. Vol. 93, 14503–14508); HDAC2/YY-1BP (Yang, W. M. et al., Proc. Natl. Acad. Sci. USA. Vol. 93, 12845–12850; Lusser, A. et al., Science Vol. 277, 88–91, 1997); and HDAC3 (Yang, W. M. et al., J. Biol. Chem. Vol. 272, 28001–28007). HDAC1/RPD3 (Genbank Accession#: U50079) and HDAC3 (Genbank Accession#: U66914) among them were amplified and isolated by RT-PCR. Primers comprising the following nucleotide sequences were used for the PCR.

(a) Primers

<Primers for Amplifying HDAC1/RPD3>
Forward primer (HD1F): 5'-CGCGGATCCATGGCGCAGACGCAGGGCACC-3' (SEQ ID NO: 3)

(The three nucleotides, "CGC", at the 5' end were added to facilitate restriction enzyme reaction. The segment, "GGATCC", from the 4th nucleotide to the 9th nucleotide at the 5' end corresponds to a site for restriction enzyme BamHI.)

Reverse primer (HD1R) : 5'-CGCCTCGAGGGCCAACTTGACCTCCTCCTT-3' (SEQ ID NO: 4)

(The three nucleotides, "CGC", at the 5' end were added to facilitate restriction enzyme reaction. The segment, "CTCGAG", from the 4th nucleotide to the 9th nucleotide at the 5' end corresponds to a site for restriction enzyme XhoI.)

The DNA encoding the first amino acid residue to 482nd residue of HDAC1/RPD3 (full length) was amplified with this primer set.

<Primers for Amplifying HDAC3>
Forward primer (HD3F): 5'-CGCGGATCCATGGCCAAGACCGTGGCGTAT-3' (SEQ ID NO: 5)

(The three nucleotides, "CGC", at the 5' end were added to facilitate restriction enzyme reaction. The segment, "GGATCC", from the 4th nucleotide to the 9th nucleotide at the 5' end corresponds to a site for restriction enzyme BamHI.)

Reverse primer (HD3R): 5'-CGCCTCGAGAATCTCCACATCGCTTTCCTT-3' (SEQ ID NO: 6)

(The three nucleotides, "CGC", at the 5' end were added to facilitate restriction enzyme reaction. The segment, "CTCGAG", from the 4th nucleotide to the 9th nucleotide at the 5' end corresponds to a site for restriction enzyme XhoI.)

The DNA encoding from the first amino acid residues to the 482nd residue of HDAC3 (full length) was amplified using the two primer pairs.

(b) Conditions of RT-PCR cDNA derived from human cervical cancer cell line HeLa cell was used as a template for the amplification of histone deacetylase gene by PCR. First, to prepare the cDNA, total RNA was extracted and purified from HeLa cells by the phenol-guanidine thiocyanate method (Nippon Gene; ISOGEN). The cDNA was synthesized from the extracted total RNA using random primer (reverse transcription). Then, PCR was carried out using this cDNA as a template under the following conditions: (1) 1 cycle of incubation at 92° C. for 3 minutes; (2) 35 cycles of denaturation at 92° C. for 1 minutes, annealing at X° C. for 1 minutes, and extension at 72° C. for 1 minutes; and (3) 1 cycle of incubation at 72° C. for 10 minutes. The annealing temperature (X° C.) was selected for respective primer sets for respective genes as described below: the combinations of primer set/annealing temperature are HD1F-HD1R/64° C. and HD3F-HD3R/64° C. A thermostable DNA polymerase, Pfu-Turbo polymerase (Stratagene), was used in the PCR.

(c) Subcloning of the PCR products into an expression vector and confirmation of nucleotide sequences DNA band of each product amplified by PCR was confirmed by electrophoresis on 1% agarose gel. After confirmation of the presence of the band, each of the PCR products were digested with restriction enzymes BamHI and XhoI. By this treatment, the DNA was digested at the restriction enzyme sites that had been introduced at the 5' end of each PCR primer, and thus the PCR products were converted to have cohesive ends at both ends. The respective PCR products treated with the restriction enzymes were separated by agarose gel electrophoresis. Gel pieces containing respective bands of PCR products separated on the agarose gel were cut out, and the PCR products were separated and purified from the agarose gel with glass milk (Bio-101). The PCR products separated and purified from the agarose gel were subcloned into the cloning sites of expression vectors pCMV-8XHis and pCMV-Flag. pCMV-8Xhis and pCMV-Flag are vectors constructed by inserting at the restriction sites, XhoI/XbaI of pcDNA3 (Invitrogen), adapter oligonucleotides that encode 8XHis and Flag, respectively, described below.

pCMV-8Xhis:

```
                                         (SEQ ID NO: 7)
C-8XHis upper:  5'-TCGAGCTAGCACATCACCACCATCACCATCAT
                                              CACTAAG-3'

(SEQ ID NO: 8)
C-8XHis lower:  5'-CTAGCTTAGTGATGATGGTGATGGTGGTGATG
                                              TGCTAGC-3'
``` pCMV-Flag:

```
                                         (SEQ ID NO: 9)
C-Flag upper:   5'-TCGAGGGGGACTATAAGGACGATGATGATGAT
                                              AAATAAT-3'
```

-continued

C-Flag lower: 5'-CTAGATTATTTATCATCATCATCGTCCTTATA
GTCCCCC-3' (SEQ ID NO: 10)

Each of the expression vectors was pre-digested with the restriction enzymes, BamHI and XhoI, the same as those used to digest the ends of the PCR products to separate and purify on agarose gel. The PCR products and the expression vector were mixed at a molar ratio nearly 1:1. Ligation was carried out with T4 ligase at 16° C. for 1 hour. After the ligation, each sample was introduced into *E. coli* DH5α that were converted to competent cells by the rubidium chloride method. The cells were plated on LB plates containing selection antibiotic, 50 µg/ml ampicillin. The plates were incubated at 37° C. overnight. A number of colonies were picked up from the plate and were cultured overnight in LB-ampicillin media. Plasmids (the expression vectors) were purified from the cultured *E. coli* cells by the alkali method. The plasmids were digested with restriction enzymes BamHI and XhoI, and the presence of the inserts (PCR products) was confirmed by agarose gel electrophoresis. The nucleotide sequences of the inserts in the plasmids were determined with automatic sequencer, and were confirmed to have the same sequence as those previously reported.

(2) Isolation of Cell Lines Producing Recombinant Histone Deacetylase 2.5 µg of each of the expression vectors, pCMV-8X His-HDAC1, pCMV-Flag-HDAC1, pCMV-8XHis-HDAC3, and pCMV-Flag-HDAC3 constructed in (1) was transfected into CHO cells by the lipofection method. The cells were cultured in culture media containing 500 µg/ml geneticin for about 2 weeks to select neomycin-resistant clones. 12 clones were independently isolated, and cultured in 24-well plates. Then, clones introduced with the genes and expressing the histone deacetylases were identified by Western blotting using anti-His-Tag antibody and anti-Flag antibody, and antibody against respective histone deacetylases.

(3) Purification of Recombinant Histone Deacetylase (a) pCMV-8XHis-HDAC 8 continuous histidine (8His-Tag) were added to the carboxyl terminus of the recombinant protein by using the pCMV-8Xhis vector. The recombinant protein was purified utilizing the complex formation between the 8His-Tag and nickel. $1 \times 10^9$ cells that produce recombinant histone deacetylase were well suspended in a hypotonic buffer, and allowed to stand on ice for 30 minutes. Then, nuclear fraction was obtained from the suspension by centrifugation at a low speed. After washing the nuclear fraction twice with hypotonic buffer, extraction buffer was added thereto. The sample was sonicated and then centrifuged at a high speed. Soluble nuclear fraction containing the recombinant protein was obtained from the supernatant. The soluble nuclear fraction was loaded on Ni-NTA-agarose column (Qiagen) to adsorb the recombinant protein on the column via 8His-Tag. The column was washed well with extraction buffer, and then further washed with wash buffer. The recombinant protein was eluted with elution buffer. The elution was conducted by increasing the imidazole concentration stepwise (50 mM, 100 mM, 200 mM, and 1 M). Fractions containing the recombinant histone deacetylase were pooled and dialyzed against a sufficient volume of HDAC buffer overnight. The recombinant histone deacetylase solution was stored at −80° C. The composition of each buffer was as follows.

Hypotonic Buffer:
  10 mM Hepes KOH, pH 7.5
  10 mM KCl
  10 mM $MgCl_2$
  0.1% NP-40

Extraction Buffer:
  20 mM Tris-HCl, pH 7.9
  5 mM imidazole
  0.5 M NaCl

Wash Buffer:
  10 mM imidazole
  0.5 M NaCl
  20 mM Tris-HCl, pH 7.9

Elution Buffer:
  50 mM to 1 M imidazole
  0.5 M NaCl
  20 mM Tris-HCl, pH 7.9

HDAC Buffer:
  20 mM Hepes KOH, pH 7.5
  150 mM NaCl
  1 mM EDTA
  50% glycerol (b) pCMV-Flag-HDAC An epitope tag, Flag-Tag, was added to the carboxyl terminus of the recombinant protein by using the pCMV-Flag-HDAC vector. The recombinant protein was purified by a method using anti-Flag-Tag (M2) antibody column that utilizes the binding between anti-Flag-Tag antibody and Flag-Tag. Soluble nuclear fraction was prepared according to the same method as described above, and was diluted 3-fold with cold distilled water. The solution was loaded on the anti-Flag-Tag (M2) antibody column (Sigma) to adsorb the recombinant protein on the column via the Flag-Tag. The column was washed well with wash buffer, and the protein was eluted with elution buffer containing 250 µg/ml Flag peptide (Asp-Tyr-Lys-Asp-Asp-Asp-Asp-Lys). Fractions containing the recombinant histone deacetylase were pooled and dialyzed against a sufficient volume of buffer overnight. The recombinant histone deacetylase solution was stored at −80° C. The composition of each buffer was as follows.

Wash Buffer:
  20 mM Tris-HCl, pH 7.5
  250 mM NaCl
  0.05% Triton X-100

Elution Buffer:
  20 mM Tris-HCl, pH 7.5
  150 mM NaCl
  10% glycerol
  1 mM EDTA

EXAMPLE 2

Partial Purification of Histone Deacetylase from Human Culture Cell Line

MCF7 cells were washed with PBS, and then centrifuged. Precipitated cells were suspended in 4 ml lysis buffer and were left standing 15 minutes on ice. 5 ml lysate buffer was obtained by washing the centrifuge tube with 1 ml lysis buffer. The lysate was loaded on 15 ml sucrose cushion buffer in a centrifuge tube for type-07 rotor. Then, The tubes were centrifuged at 1300 g for 20 minutes and precipitated cells were recovered with 1.5 ml of the lysis buffer. After washing the cells, the cells were suspended in 700 μl low-salt buffer. The cells were sonicated for 30 seconds, and then allowed to stand still on ice for 30 minutes. The lysate was centrifuged at 100, 000 g for 40 minutes, and the supernatant was collected to recover crude histone deacetylase. The pooled crude histone deacetylase was placed in a 1.5-ml tube, and was dialyzed overnight against a solution containing 50% glycerol, 150 mM NaCl, and 20 mM Tris (pH 7.5). The dialysate was substituted 3 times with fresh buffer. The partially purified histone deacetylase prepared by the above-mentioned procedure was used for measuring the deacetylase activity. The composition of each buffer was as follows.

Sucrose Cushion Buffer:
  30% sucrose
  10 mM Tris (pH 7.5)
  10 mM NaCl
  3 mM $MgCl_2$ Lysis Buffer:
  10 mM Tris (pH 7.5)
  10 mM NaCl
  15 mM $MgCl_2$
  0.1 mM EGTA
  250 mM sucrose
  0.45% NP-40
  0.1 mM PMSF Low-salt Buffer:
  50 mM Hepes (pH 7.5)

EXAMPLE 3

Measurement of the Deacetylase Activity (1) Substrate Peptide
Boc-Val-Leu-(Ac)Lys-MCA The substrate peptide was prepared by condensing the amino group of the fluorescent substance AMC (7-amino-4-methyl-coumarin) and the carboxyl group of a peptide comprising a lysine with acetylated -amino group. The peptide was prepared by custom synthesis by PEPTIDE INSTITUTE, INC.

(2) Measurement Procedure
1 μl of DMSO solution containing 10 mM substrate peptide, Boc-Val-Leu-(Ac) Lys-MCA, was added to 64 μl HDAC reaction buffer (25 mM Tris-HCl, pH 7.5) for each assay. The mixture was poured into the wells of a microplate for fluorometry and was incubated at 30° C. Then, 10 μl of histone deacetylase solution was added to each well and the plate was subjected for deacetylation at 30° C. for 60 minutes. After the reaction, 5 μl of peptidase solution that was diluted with 25 mM Tris-HCl (pH 7.5) to an optimal concentration and 20 μl 5× protease reaction buffer were added to each well. The fluorescence intensity was measured every 150 seconds with fluorescence microplate reader. The fluorescence intensity was measured using Wallac 1420 ARVOsx Multi Label Counter (Amersham-Pharmacia Biotech). The composition of the reaction buffer was as follows.

5× Protease Reaction Buffer:
  500 mM Tris-HCl, pH 9.6
  50 mM β-mercaptoethanol (3) Result of the Measurement
The activities of the deacetylase in the fraction of histone deacetylase partially purified from human culture cell line and the recombinant histone deacetylase were assayed according to the above method. The result is depicted in FIGS. 1 to 5.

Figure 2:
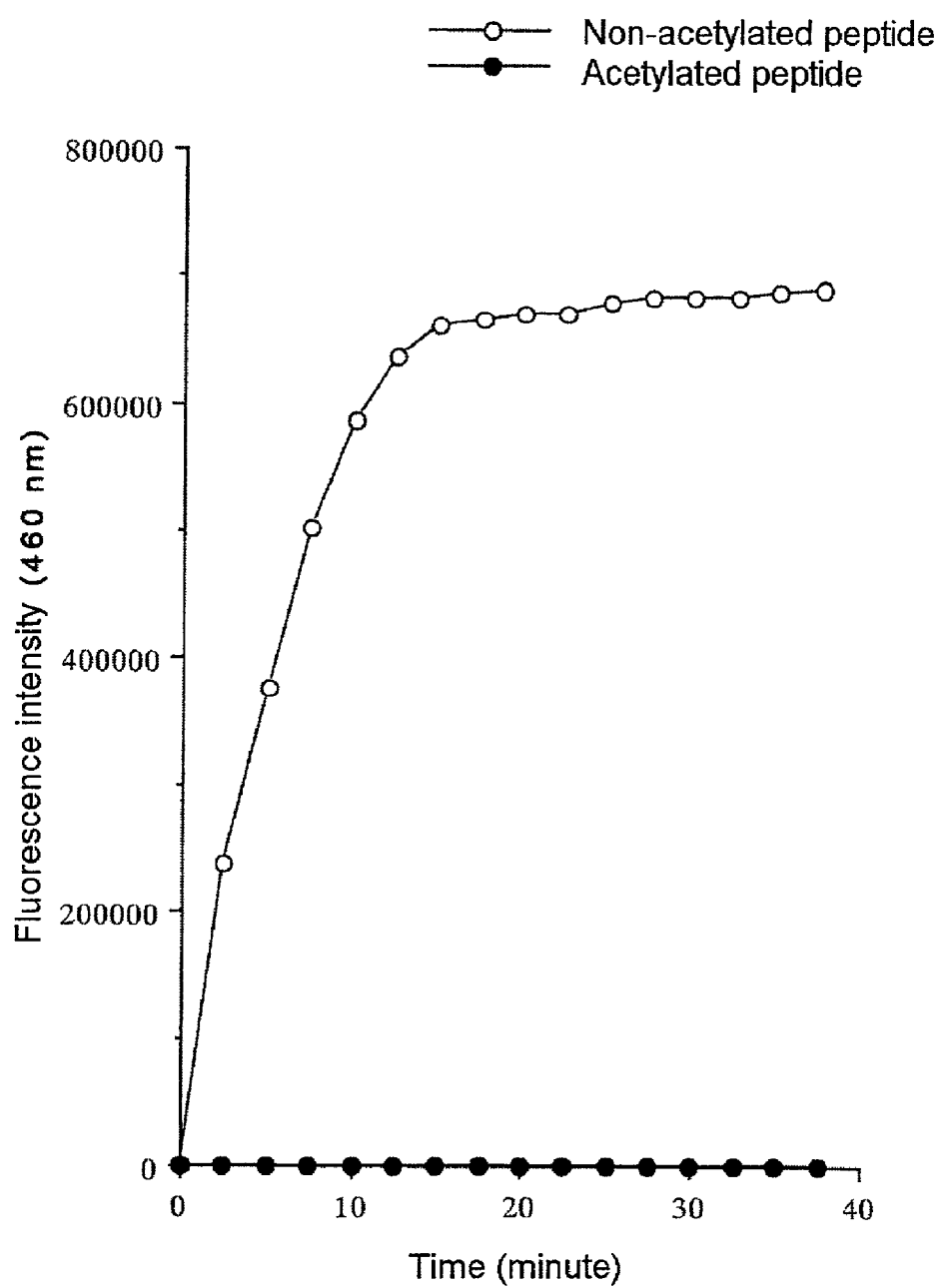
FIG. 2 depicts a graph comparing the peptide cleavage activity of plasmin using acetylated or non-acetylated peptides as the substrate.

The comparison of the cleaving activities of lysylendopeptidase and plasmin against the fluorescence labeled substrate peptides, Boc-Val-Leu-Lys-MCA and Boc-Val-Leu-(Ac) Lys-MCA (with an acetylated lysine residue), is demonstrated in FIG. 1 and 2.

$5\times10^{-6}$ AU lysylendopeptidase or 0.001U plasmin was added to Boc-Val-Leu-Lys-MCA or Boc-Val-Leu-(Ac)Lys-MCA. The Figures show the fluorescence intensity measured at an interval of about 150-seconds. Both lysylendopeptidase and plasmin digested Boc-Val-Leu-Lys-MCA, but did not cleave Boc-Val-Leu-(Ac)Lys-MCA whose lysine residue had been acetylated.

Figure 3:
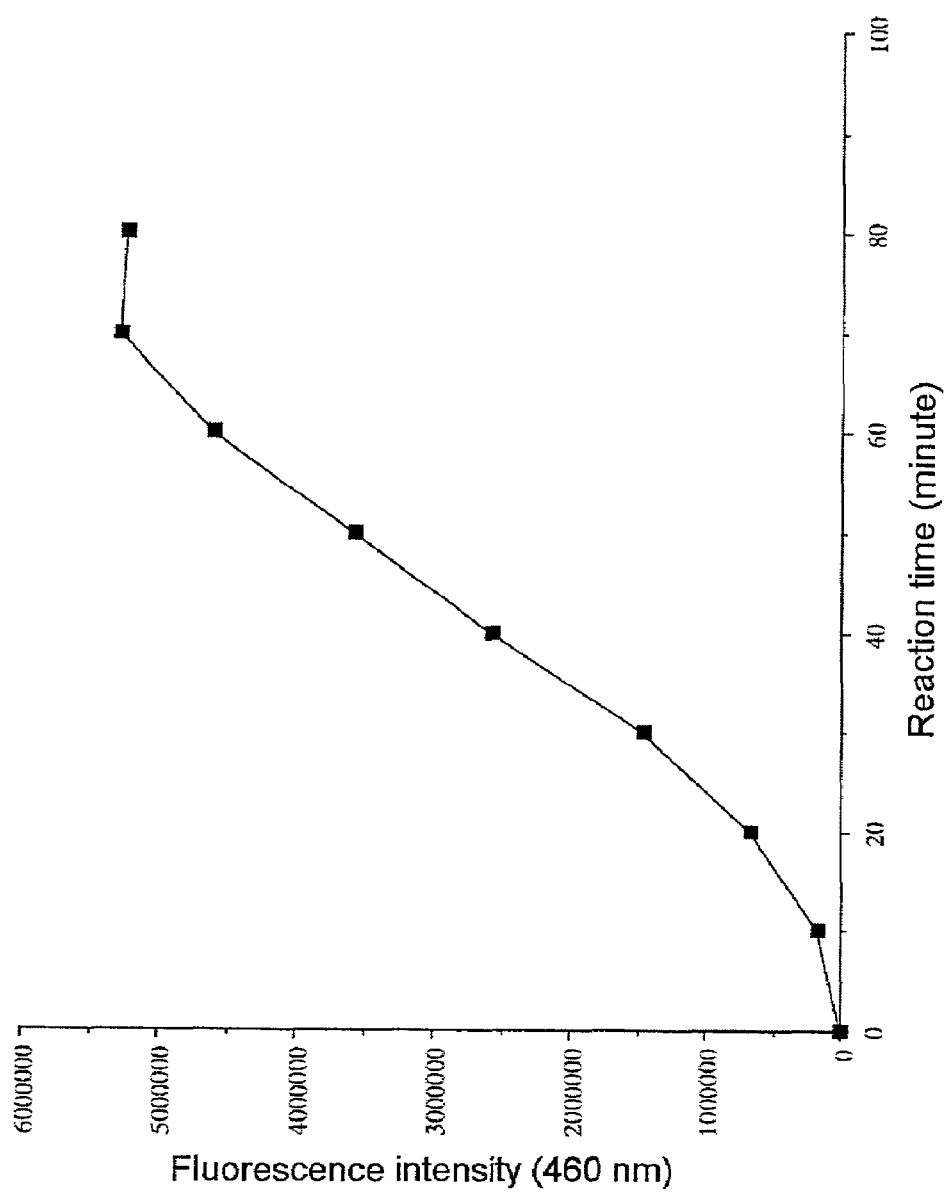
FIG. 3 depicts a time course of the deacetylation reaction.

FIG. 3 shows a time course of deacetylation. Boc-Val-Leu-(Ac)Lys-MCA was deacetylated, and then $5\times10^6$ AU lysylendopeptidase was added thereto. This Figure demonstrates the fluorescence intensity after the proteolytic reaction reached plateau (after about 20 minutes). The fluorescence intensity was demonstrated to increase depending on the time of deacetylation.

Figure 4:
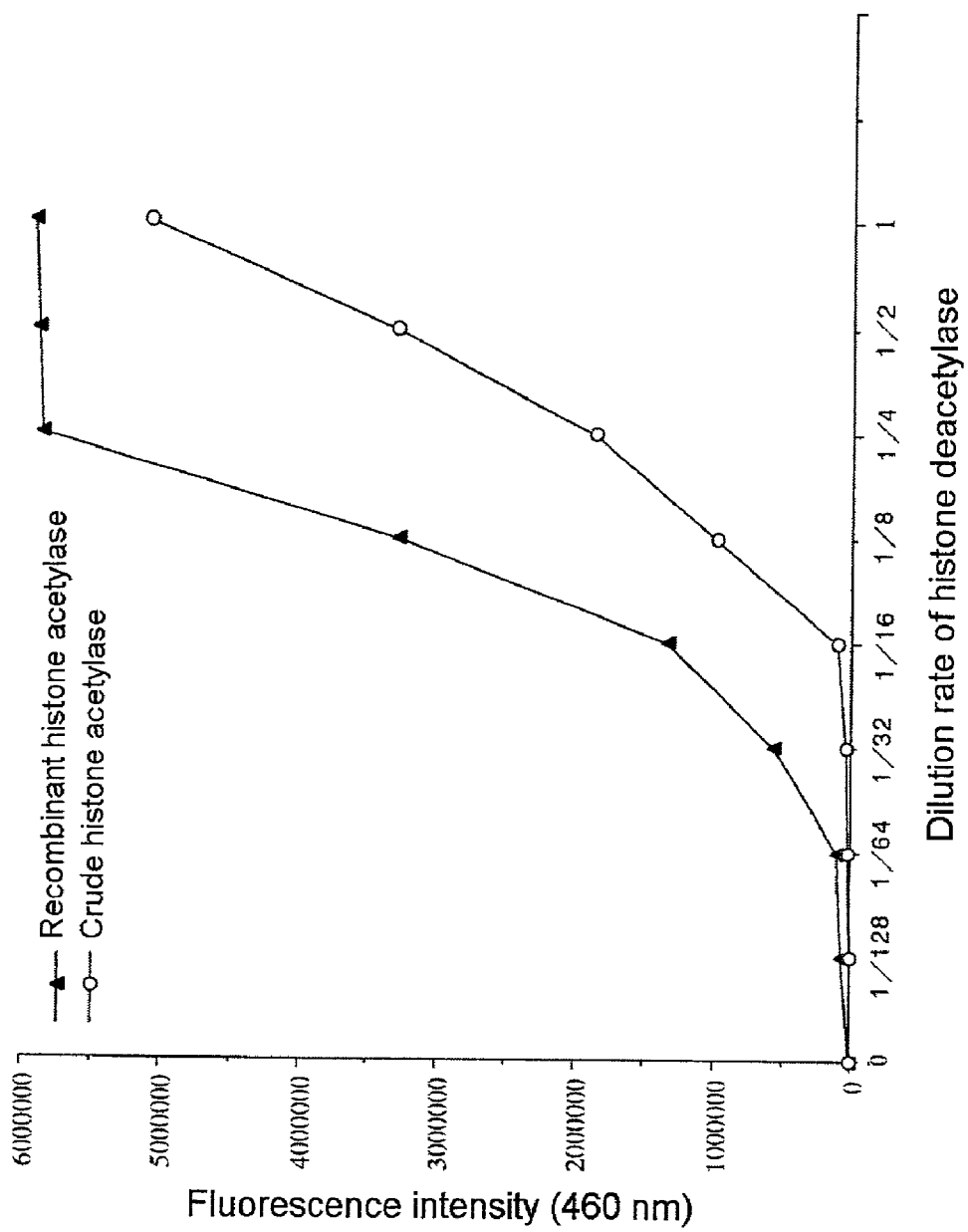
FIG. 4 depicts a graph demonstrating the dose-dependency of the deacetylase in the deacetylation reaction.

FIG. 4 shows the enzyme dose-dependency of the deacetylation reaction. The original solutions of recombinant histone deacetylase and crude histone deacetylase were respectively diluted 4-fold to subject them to deacetylation. Then, $5\times10^{-6}$ AU lysylendopeptidase was added thereto. This Figure shows the fluorescence intensity after the proteolytic reaction reached plateau (after about 20 minutes). The fluorescence intensity was demonstrated to increase depending on the quantity of histone deacetylase.

Figure 5:
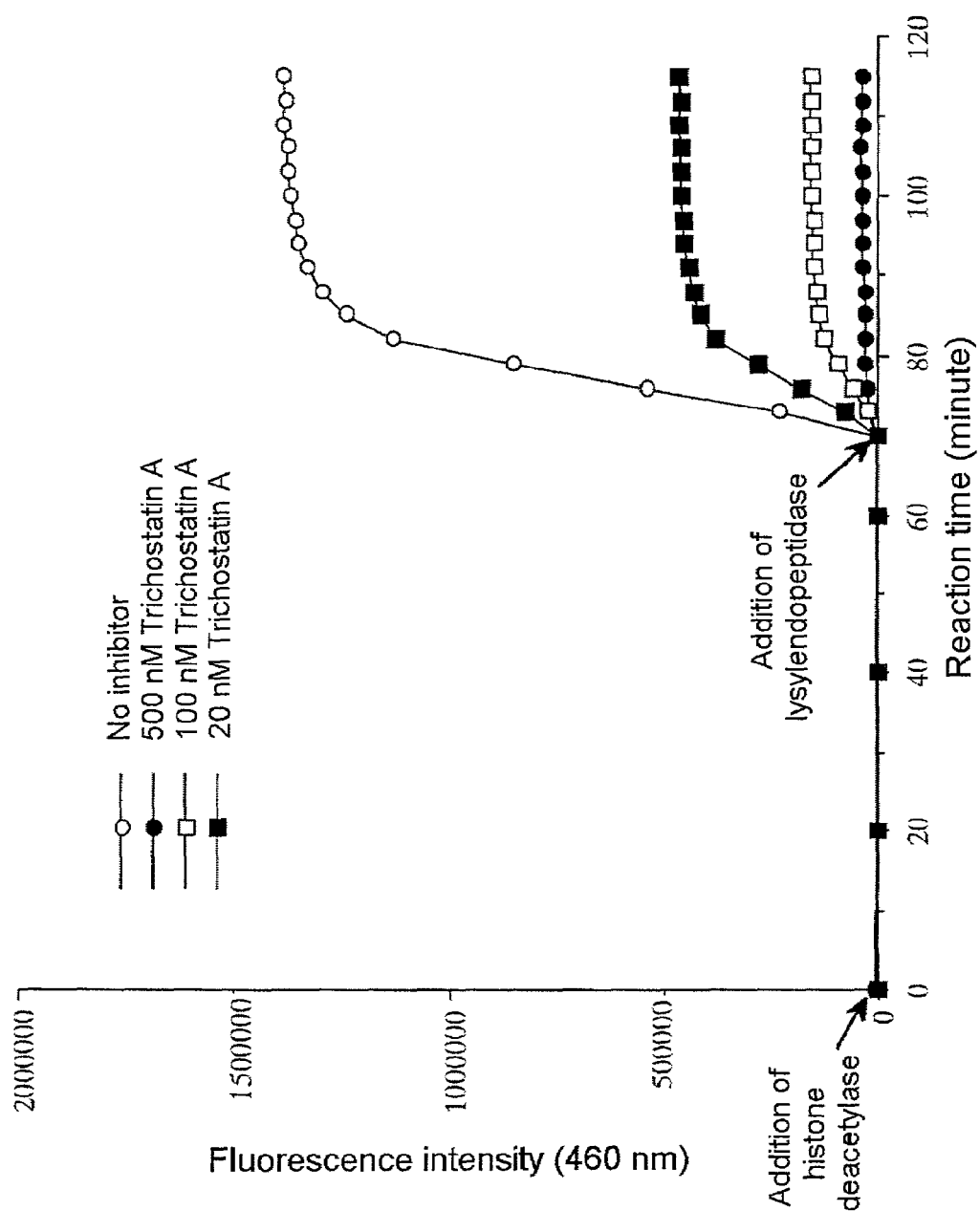
FIG. 5 depicts a graph demonstrating the result of measurement according to the present invention, wherein the effect of the histone deacetylase inhibitor, Trichostatin A, on the deacetylation is measured.

FIG. 5 shows the effect of a known histone deacetylase inhibitor, Trichostatin A. Trichostatin A was added to the deacetylation reaction solution at the concentrations indicated in the figure to determine its effect on the reaction. Trichostatin A almost completely inhibited the reaction at a concentration of about 200 nM. The method of the present invention was demonstrated to provide a safe method for measuring the activity of histone deacetylase.

EXAMPLE 4

Establishment of an Assay System for the Activity of SIRT1 using FMAP (Fluorometric Assay with Proteinase)

In 2000, it was reported that yeast and nematoda Sir2, associated with gene silencing and aging, were NAD-dependent histone deacetylases. The present inventors expressed and purified recombinant protein of SIRT1, which was a human Sir2 homologue, and demonstrated that the activity of NAD-dependent protein-deacetylating enzyme could be detected using a newly established assay system for the deacetylase activity. It was then reported that SIRT1 suppressed the activity of the tumor suppressor gene product p53 through deacetylating p53 acetylated after DNA damages. A SIRT1 inhibitor is expected to enhance the p53 function more strongly when used in combination with an agent capable of inducing DNA damages; such an inhibitor is a potential effective anti-cancer agent. The use of the assay system established herein by the present inventors for the deacetylase activity provides the way to the achievement of rapid and low-cost screening of an enormous number of compounds of chemical library.

1. Isolation of the Gene for the Novel Histone Deacetylase SIRT1 by RT-PCR

The following PCR primers were prepared to isolate, by RT-PCR, the gene for the deacetylase SIRT1 (human Sir2 homologue), which was reported to be a novel deacetylase distinct from the previously found histone deacetylase.

(1) PCR Primers for the SIRT1 gene
Forward primer (SIRT1F): 5'-ATAGGATCCCAGAGAG-GCAGTTGGAAGATG -3' (SEQ ID NO: 11)

(The three nucleotides, "ATA", at the 5' end were added to facilitate restriction enzyme reaction. The segment from the 4th nucleotide to the 9th nucleotide at the 5' end corresponds to a site for restriction enzyme BamHI.)
Reverse primer (SIRT1R): 5'-CGCGTCGACT-GATTTGTTTGATGGATAGTT -3' (SEQ ID NO: 12)

(The three nucleotides, "CGC", at the 5' end were added to be facilitate restriction enzyme reaction. The segment from the 4th nucleotideto 9th nucleotide at the 5' end corresponds to a site for restriction enzyme SalI.)

The DNA encoding for the first amino acid residue to the 747th residue of SIRT1 (full length) was amplified using this primer set.

(2) Conditions of RT-PCR

A human placental cDNA library was used as the template in the PCR amplification. PCR was carried out under the following conditions: (1) 1 cycle of incubation at 92° C. for 3 minutes; (2) 35 cycles of denaturation at 92° C. for 1 minute, annealing at 66° C. for 1 minute, and extension at 72° C. for 1 minute; and (3) 1 cycle of incubation at 72° C. for 10 minutes. The thermostable DNA polymerase used in PCR was Pfu-Turbo polymerase (Stratagene).

(3) Construction of an Expression Vector for Recombinant SIRT1

DNA band of each product amplified by PCR was confirmed by electrophoresis on 1% agarose gel. After confirmation of the presence of the band, each of the PCR products were digested with restriction enzymes BamHI and SalI. By this treatment, the DNA was digested at the restriction enzyme sites that had been introduced at the 5' end of each PCR primer, and thus the PCR products were converted to have cohesive ends at both ends. The respective PCR products treated with the restriction enzymes were separated by agarose gel electrophoresis. Gel pieces containing respective bands of PCR products of desired sizes were cut out, and the PCR products were separated and purified from the agarose gel with glass milk. The PCR products separated and purified from the agarose gel were subcloned into the cloning sites of *E. coli* expression vector pGEX-4T-1. pGEX-4T-1 that had been digested in advance with the restriction enzymes, BamHI and SalI, the same as those used to digest the ends of the PCR products, and that had been separated and purified on agarose gel was used. The PCR products and pGEX-4T-1 were mixed together at a molar ratio of nearly 1:1. Ligation was carried out with T4 ligase at 16° C. for 1 hour. After the ligation, the PCR product and pGEX-4T-1 were introduced into *E. coli* DH5α that were converted to competent cells by the rubidium chloride method. The cells were plated on LB plates containing selection antibiotic, 50 μg/ml ampicillin. The plates were incubated at 37° C. overnight. A number of colonies were picked up from the plate and were cultured overnight in LB-ampicillin media. Plasmids (the expression vector) were purified from the cultured *E. coli* cells by the alkali method. The plasmids were digested with appropriate restriction enzymes, and the presence of the inserts (PCR products) was confirmed by agarose gel electrophoresis. The nucleotide sequences of the inserts in the plasmids were determined with automatic sequencer. Plasmids containing an insert having the identical nucleotide sequence to that of the reported SIRT1 were selected. Thus, the construction of pGEX-4T-1/SIRT1 was completed.

2. Expression and Purification of Recombinant SIRT1

(1) Induction of Expression of Recombinant SIRT1

In order to express and purify the recombinant SIRT1, the *E. coli* expression vector pGEX-4T-1/SIRT1 was introduced into the host *E. coli* strain BL21 Gold (DE3) for expression. The cells of BL21 Gold (DE3) containing the expression vector were inoculated to LB medium containing 50 μg/ml ampicillin and incubated at 37° C. overnight. 10 ml of the *E. coli* pre-culture was then inoculated to 1 liter of LB medium containing 50 μg/ml ampicillin and cultured at 37° C. When OD at 600 nm reached 0.8, IPMG was added at a final concentration of 1 mM. Then, the culture was continued for 4 hours, and thus the expression of recombinant SIRT1 was induced. The cells of *E. coli* expressing the recombinant were harvested as cell pellet by centrifugation.

(2) Purification of Recombinant SIRT1

GST protein derived from the pGEX4T-1 vector was fused to the amino terminal end of the recombinant SIRT1. The recombinant SIRT1 was purified by using the binding of GST and GSH. The harvested *E. coli* cells were well suspended in a lysis buffer (PBS containing 1% TritonX-100, 1 mM PMSF, 1 mM benzamidine, 2 μg/ml pepstatin A, and 5 μg/ml leupeptin), and sonicated on ice for about 5 minutes to lyse the cells completely. The lysate was treated by high-speed centrifugation, and the supernatant was saved as soluble fraction. The soluble fraction was loaded onto GSH column, and the recombinant SIRT1 contained in the lysate was adsorbed on the column via GST. The GSH column was washed sufficiently with lysis buffer, and then the recombinant SIRT1 was eluted from the GSH column with elution buffer (10 mM CSH, 50 mM Tris-HCl). The presence of the recombinant SIRT1 in some eluted fractions was confirmed with a spectrophotometer. The fractions were combined together and dialyzed against a sufficient volume of a dialysis buffer (150 mM NaCl, 50% Glycerol, and 20 mM Tris-HCl). The dialysis was continued until the recombinant SIRT1 solution reached a complete equilibrium state. The recombinant SIRT1 solution was stored at −80° C. until it was used.

3. Detection of the Deacetylation Activity of SIRT1 According to the Principle of FMAP (1) Substrate Peptide It has been reported that yeast Sir2 (SIRT1 is the human Sir2) specifically deacetylates histone H4 on the acetylated lysine at the 16th amino acid residue. A peptide was synthesized that consisted of (1) the amino acid sequence from the 13th amino acid residue to the 20th amino acid residue of Tetrahymena histone H4, which had been used in this report, (2) the fluorescent substance Nma attached to the amino terminus of the amino acid sequence, and (3) the quenching substance Dnp attached to its carboxy-terminus via a lysine residue.

Peptide for the SIRT1-activity assay:
Nma-VGAK(Ac)RHSK(Dnp)-NH2

(The sequence derived from the Tetrahymena histone H4 was used in this Example, but as a matter of course the human or yeast histone H4 is expected to give a similar result as well. Thus, there is no limitation on the type of histone H4 sequence. Further, a recent report also showed that SIRT1 can deacetylate the tumor suppressor gene product p53, and the use of this target sequence is predicted to give a similar result.)

Besides, the amino acid sequences of this region are identically conserved from plasmodial slime mold to human.
Human: GGAKRHRK (14–21)
Plasmodial slime mold Physarum polycephalum: GGAKRHRK (13–20)
Nematoda Caenorhabditis elegans: GGAKRHRK (29–36)
Starfish Asteroidea: GGAKRHRK (14–21)

(2) Measurement Procedure

5 µl of 0.005 U/µl lysylendopeptidase (LEP) was combined with 90 µl of an enzyme reaction buffer (50 mM Tris-HCl (pH 8.8), 4 mM $MgCl_2$, 0.2 mMDTT) and 1 µl of 10 mMpeptide solution for SIRT1-activity assay. 2 µl of 5 mM NAD and 2 µl of each of serial dilutions of a recombinant SIRT1 solution, or alternatively 2 µl of each of serial dilutions of an NAD solution and 2 µl of a solution containing 1 mg/ml recombinant SIRT1 were added at the same time to the mixture. The enzyme reaction and fluorescence assay were performed at 30° C. using 384-well plates for fluorescence assay.

The fluorescence intensity was measured at excitation wavelength 355 nm/fluorescence wavelength 460 nm by using a Wallac 1420 ARVO HTS Multi Label Counter. The measurement was repeated at about 2- to 3-minute intervals for 50 minutes.

(3) Result of the Measurement

The result of the measurement for the deacetylase activity of recombinant SIRT1 is shown below; the recombinant was expressed in E. coli and purified by the method described above.

Figure 6:
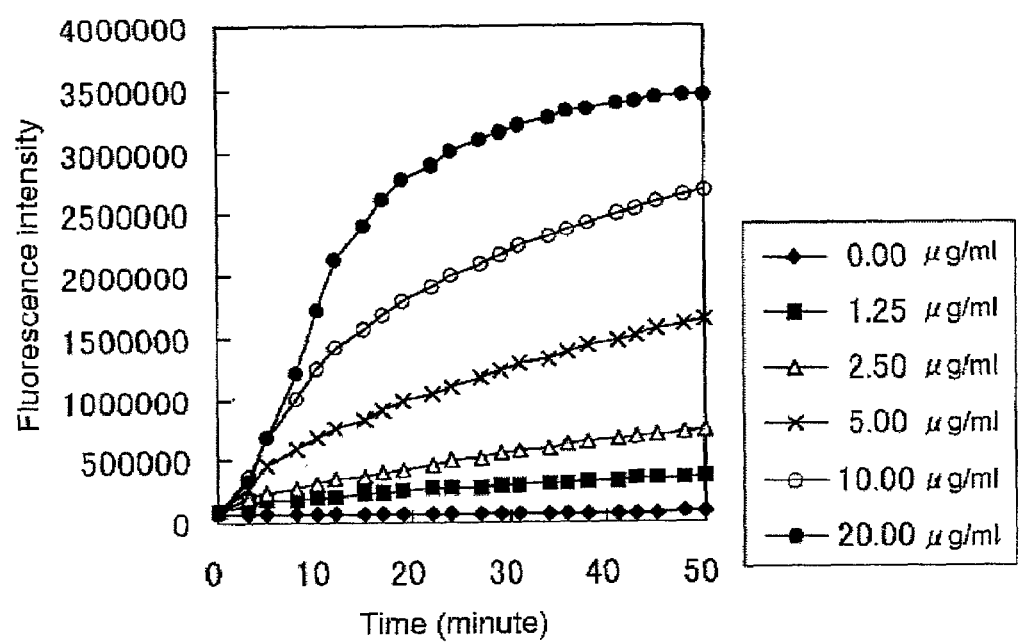
FIG. 6 shows the recombinant SIRT1 concentration-dependent increase in the fluorescence intensity in the deacetylation reaction.

FIG. 6. The recombinant SIRT1 Concentration-dependent Increase in the Fluorescence Intensity in the Deacetylation Reaction A recombinant SIRT1 solution was diluted serially, and each was added to the reaction solution to observe differences in the fluorescence intensity. The result showed that the fluorescence intensity increased was proportional to the recombinant SIRT1 concentration. In the absence of recombinant SIRT1, the fluorescence intensity did not increase, namely, the fluorescent substrate was not cleaved off by LEP at all. Accordingly, it was clarified that the deacetylation by the recombinant SIRT1 led to the cleavage of the fluorescent substrate by LEP.

Figure 7:
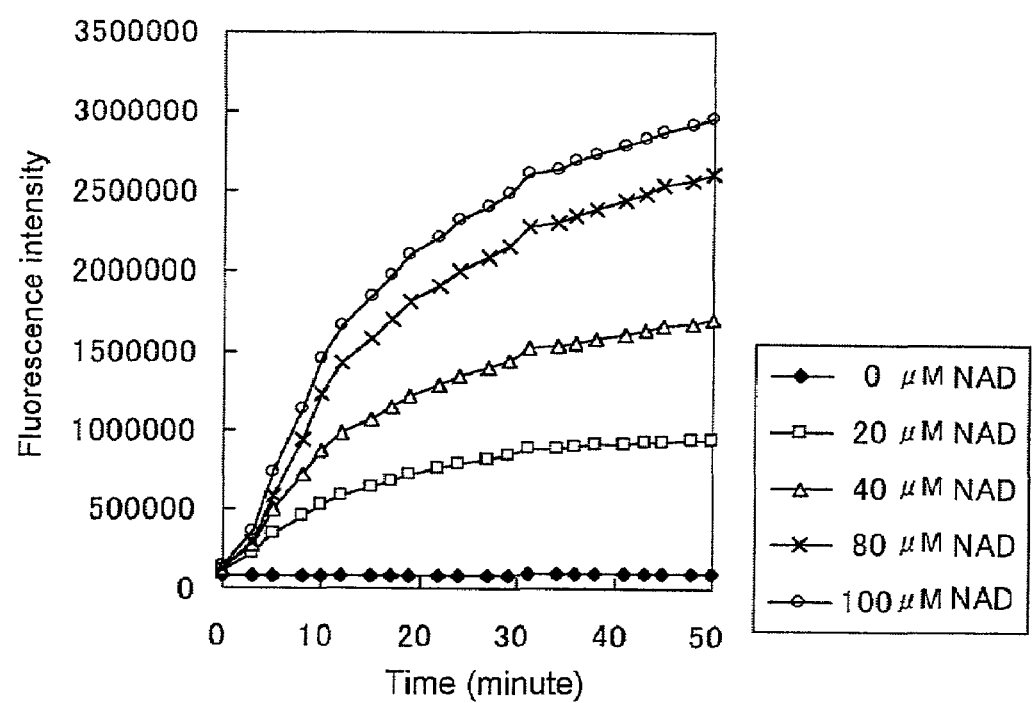
FIG. 7 shows detection of NAD concentration-dependent changes in the deacetylation activity of the recombinant SIRT1.

FIG. 7. Detection of NAD Concentration-dependent Changes in the Deacetylation Activity of the Recombinant SIRT1

It has been reported that the presence of NAD is essential for the deacetylase activity of SIRT1. In order to assess whether the NAD-dependency of SIRT1 activity can be detected using the assay method, an NAD solution was serially diluted and each dilution was added to the reaction solution, and then observation was made for the changes in the fluorescence intensity. The result showed that the fluorescence intensity increased in an NAD concentration-dependent fashion. In the absence of NAD, regardless of the presence of the recombinant SIRT1, the fluorescence intensity did not increase, namely, the cleavage of fluorescence substrate by LEP was not detectable at all. Thus, it was demonstrated that, with this assay system, the NAD-dependent SIRT1 activity could be assayed very precisely as expected based on the report, and the system exhibited high performance to detect substances, such as NAD, enhancing the enzyme activity, and substances inhibiting the activity.

4. Concluding Remarks

As seen in the figures, a simple assay system for the activity of the novel deacetylase SIRT1 was successfully established based on the methodological principle using altered cleavage specificity of a peptidase. Furthermore, the NAD-dependent SIRT1 activity was successfully detected very accurately with this system.

Substances inhibiting or enhancing the activity of SITR1 deacetylase can be selected by simply adding, to the enzyme reaction according to this assay system, various chemical substances, extracts from natural material, culture supernatants of cells and bacteria, and so on. In addition, the system is usable to evaluate the selectivity of agents inhibiting or enhancing the deacetylase activity in comparative assay comprising this system and the histone deacetylase assay system.

INDUSTRIAL APPLICABILITY

The present invention provides methods for determining the acetylation levels of a peptide, methods for measuring deacetylase activity, and methods of screening for deacetylase inhibitors or accelerators. The basic principle of the present invention is to convert the degree of deacetylation to the level of peptidase activity which is conducted following the deacetylation. The principle is applicable not only to deacetylases but also to acetylases. Conventional methods for measuring peptidase activity are very simple and can be carried out at low costs. Further, the reaction of the present methods can be performed in a single container, and thus, the measurement for the activities can be conducted continuously. Accordingly, great improvement of efficiency in the measurement for deacetylase activity and screening for inhibitors, and such can be achieved according to these methods. Thus, the present invention is expected to largely contribute to new drug discovery.

The present inventors filled a patent concerning methods which do not utilize radioisotopes and detect the activity of deacetylases that uses antibodies specifically binding to acetylated peptides (WO 99/36532). B/F separation is required in the detection of deacetylase activity by ELISA according to this method. Thus, multiple steps are necessary for the treatment to achieve this reaction, which makes it difficult to continuously measure the activity. The method for measuring the deacetylase activity according to the present invention can be carried out with much more convenience, as compared to the prior method.

Substances inhibiting deacetylase are demonstrated to arrest cell cycle and induce cell differentiation (Taunton, J. et al., Science Vol. 272, 408–411, 1996; Yoshida, M. et al., J. Biol. Chem. Vol. 265, 17174–17179, 1990; Kijima, M. et al., J. Biol. Chem. Vol. 268, 22429–22435, 1993; Chen, W. Y. et al., Proc. Natl. Acad. Sci. USA. Vol. 94, 5798–5803, 1997; Medina, V. et al., Cancer Res. Vol. 57, 3697–3707, 1997). Thus, such substances are expected to act as anticancer agents and antimicrobial substances, which prospectively increases their importance. Therefore, the present invention has a great meaning in establishing a convenient method of screening for such substances.

The invention claimed is:

1. A method for determining an acetylation level of a substrate peptide, comprising:
   (a) contacting a substrate peptide labeled with a substance which emits a signal with a peptidase whose peptide-cleaving activity changes upon the acetylation level of the peptide; and
   (b) measuring a quantity of the substrate peptide cleaved by the peptidase based on the signal generated upon cleavage of the substrate peptide by the peptidase, wherein said quantity of the substrate peptide cleaved by the peptidase indicates the acetylation level of the substrate peptide, so that the acetylation level of the substrate peptide is determined.

2. A method for determining a deacetylation activity of a sample containing a deacetylase, comprising:
   (a) contacting a substrate peptide labeled with a substance which emits a signal with the sample containing the deacetylase under a condition necessary for deacetylation by the deacetylase; and
   (b) contacting the substrate peptide of step (a) with a peptidase whose peptide-cleaving activity changes upon an acetylation level of the substrate peptide; and
   (c) measuring a quantity of the substrate peptide cleaved by the peptidase of step (b) based on the signal generated upon cleavage of the substrate peptide by the peptidase, wherein said quantity of the substrate peptide cleaved by the peptidase indicates the acetylation level of the substrate peptide and wherein said acetylation level of the substrate peptide indicates the deacetylation activity of the sample containing the deacetylase, so that the deacetylation activity of the sample is determined.

3. The method according to claim 1 or 2, wherein the peptidase is selected from the group consisting of lysylendopeptidase, endoproteinase Lys-C, plasmin, calpain, metalloendopeptidase, and *Armillaria mellea* protease.

4. The method according to claim 3, wherein the substrate peptide comprises an acetylated lysine residue.

5. The method according to claim 4, wherein the peptidase is a lysylendopeptidase.

6. The method according to claim 1 or 2, wherein the substance which emits a signal is a dye.

7. The method according to claim 6, wherein the dye is a fluorescent substance, and the signal is a fluorescent signal.

8. The method according to claim 2, wherein the deacetylase acts on an acetyl group in the ε-amino group of a lysine residue.

9. The method according to claim 8, wherein the deacetylase is histone deacetylase.

10. The method according to claim 9, wherein the histone deacetylase is selected from the group consisting of HOAC1, HDAC2, HDAC3 and Sir2.

11. A method for Identifying a compound that inhibits or enhances deacetylation activity of a deacetylase, comprising:
    (a) contacting an acetylated substrate peptide labeled with a substance which emits a signal with the deacetylase in the presence of a test compound under a condition necessary for deacetylation by the deacetylase;
    (b) contacting the substrate peptide of step (a) with a peptidase whose peptide cleaving activity changes upon an acetylation level of the substrate peptide;
    (c) measuring a quantity of the substrate peptide cleaved by the peptidase of step (b) based on the signal generated upon cleavage of the substrate peptide by the peptidase, wherein said quantity of the substrate peptide cleaved by the peptidase indicates the acetylation level of the substrate peptide and wherein said acetylation level of the substrate peptide indicates the deacetylation activity of the deacetylase; and
    (d) identifying the compound that decreases or increases the deacetylation activity of the deacetylase relative to the deacetylation activity of the deacetylase in the absence of the test compound.

12. The method according to claim 11, wherein the deacetylase acts on an acetyl group In the ε-amino group of a lysine residue.

13. The method according to claim 12, wherein the deacetylase is histone deacetylase.

14. The method according to claim 13, wherein the histone deacetylase is selected from the group consisting of HDAC1, HDAC2, HDAC3 and Sir2.

15. The method according to claim 11, wherein the peptidase is selected from the group consisting of lysylendopeptidase, endoproteinase Lys-C, plasmin, calpain, metalloendopeptidase, and *Armillaria mellea* protease.

16. The method according to claim 15, wherein the substrate peptide comprises an acetylated lysine residue.

17. The method according to claim 16, wherein the peptidase is a lysylendopeptidase.

18. The method according to claim 11, wherein the substance which emits a signal is a dye.

19. The method according to claim 18, wherein the dye is a fluorescent substance, and the signal is a fluorescent signal.

20. A method for determining an acetylation activity of a sample containing an acetylase, comprising:
 (a) contacting a substrate peptide labeled with a substance which emits a signal with the sample containing the acetylase under a condition necessary for acetylation by the acetylase;
 (b) contacting the substrate peptide of step (a) with a peptidase whose peptide-cleaving activity changes upon an acetylation level of the substrate peptide;
 (c) measuring a quantity of the substrate peptide cleaved by the peptidase of step (b) based on the signal generated upon cleavage of the substrate peptide by the peptidase, wherein said quantity of the substrate peptide cleaved by the peptidase indicates the acetylation level of the substrate peptide and wherein said acetylation level of the substrate peptide indicates the acetylation activity of the sample containing the acetylase, so that acetylation activity of the sample is determined.

21. The method according to claim 20, wherein the peptidase is selected from the group consisting of lysylendopeptidase, endoproteinase Lys-C, plasmin, calpain, metalloendopeptidase, and *Armillaria mellea* protease.

22. The method according to claim 21, wherein the substrate peptide comprises an acetylated lysine residue.

23. The method according to claim 22, wherein the peptidase is a lysylendopeptidase.

24. The method according to claim 20, wherein the substance which emits a signal is a dye.

25. The method according to claim 24, wherein the dye is a fluorescent substance, and the signal is a fluorescent signal.

* * * * *

SEQUENCE LISTING

<160> NUMBER OF SEQ ID NOS: 12

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:Artificially
      Synthesized Peptide
<220> FEATURE:
<221> NAME/KEY: MOD_RES
<222> LOCATION: (4)
<223> OTHER INFORMATION: ACETYLATION
<220> FEATURE:
<221> NAME/KEY: BINDING
<222> LOCATION: (7)
<223> OTHER INFORMATION: A quencher binds to 7th amino acid.
<220> FEATURE:
<221> NAME/KEY: BINDING
<222> LOCATION: (1)
<223> OTHER INFORMATION: A fluorescence group binds to 1st amino acid.

<400> SEQUENCE: 1

Arg Pro Gly Leu Lys Pro Lys
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:Artificially
      Synthesized Peptide
<220> FEATURE:
<221> NAME/KEY: MOD_RES
<222> LOCATION: (3)
<223> OTHER INFORMATION: ACETYLATION
<220> FEATURE:
<221> NAME/KEY: MOD_RES
<222> LOCATION: (5)
<223> OTHER INFORMATION: Xaa represents
      N3-(2,4-Dinitrophenyl)-L-2,3-Diaminopropionic
      acid.
<220> FEATURE:
<221> NAME/KEY: BINDING
<222> LOCATION: (1)
<223> OTHER INFORMATION: A fluorescence group binds to 1st amino acid.

<400> SEQUENCE: 2

Leu Pro Lys Leu Xaa Pro Arg
 1               5

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3
cgcggatcca tggcgcagac gcagggcacc                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 4
cgcctcgagg gccaacttga cctcctcctt                                        30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
cgcggatcca tggccaagac cgtggcgtat                                        30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
cgcctcgaga atctccacat cgctttcctt                                        30

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 7
tcgagctagc acatcaccac catcaccatc atcactaag                              39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 8
ctagcttagt gatgatggtg atggtggtga tgtgctagc                              39

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 9 tcgagggga ctataaggac gatgatgatg ataaataat                               39

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:Artificially
      Synthesized Sequence
```

```
<400> SEQUENCE: 10
ctagattatt tatcatcatc atcgtcctta tagtccccc                              39

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 11
ataggatccc agagaggcag ttggaagatg                                        30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 12
cgcgtcgact gatttgtttg atggatagtt                                        30
```